United States Patent
McClelland et al.

(10) Patent No.: US 7,132,242 B2
(45) Date of Patent: Nov. 7, 2006

(54) METHOD AND DEVICE FOR TARGETED DELIVERY OF MATERIALS TO SELECTED SINGLE CELLS

(75) Inventors: Paul H. McClelland, Monmouth, OR (US); John Stephen Dunfield, Corvallis, OR (US); Rosalyn H. Upson, Eugene, OR (US); Frank Chaplen, Corvallis, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 324 days.

(21) Appl. No.: 10/704,993

(22) Filed: Nov. 10, 2003

(65) Prior Publication Data

US 2005/0101019 A1    May 12, 2005

(51) Int. Cl.
*C12Q 1/68* (2006.01)

(52) U.S. Cl. .......................... 435/6; 435/461; 435/471; 435/285.3; 435/287.1; 435/6

(58) Field of Classification Search ...................... None
See application file for complete search history.

(56) References Cited

U.S. PATENT DOCUMENTS

| | | | |
|---|---|---|---|
| 5,015,580 A * | 5/1991 | Christou et al. ............ 800/267 |
| 5,225,750 A | 7/1993 | Higuchi et al. |
| 5,456,880 A | 10/1995 | Miura |
| 5,697,901 A | 12/1997 | Eriksson |
| 5,843,644 A | 12/1998 | Liotta et al. |
| 5,843,657 A | 12/1998 | Liotta et al. |
| 5,927,547 A | 7/1999 | Papen et al. |
| 6,060,315 A | 5/2000 | Holcomb et al. |
| 6,063,629 A | 5/2000 | Knoblauch |
| 6,079,283 A | 6/2000 | Papen et al. |
| 6,083,762 A | 7/2000 | Papen et al. |
| 6,090,790 A | 7/2000 | Eriksson |
| 6,112,605 A | 9/2000 | Papen et al. |
| 6,203,759 B1 | 3/2001 | Pelc et al. |
| 6,204,030 B1 | 3/2001 | Liotta et al. |
| 6,251,658 B1 | 6/2001 | Henderson et al. |
| 6,323,043 B1 * | 11/2001 | Caren et al. ................. 436/518 |
| 6,358,749 B1 | 3/2002 | Orthman |
| 6,422,431 B1 | 7/2002 | Pelc et al. |

* cited by examiner

*Primary Examiner*—James Ketter

(57) ABSTRACT

A method and device for delivering a quantity of at least one material to a selected single cell in a manner that permits impingement of material with the cell. The material travels at a suitable trajectory and velocity and is ejected from an electronically controllable fluid device.

44 Claims, 1 Drawing Sheet

METHOD AND DEVICE FOR TARGETED DELIVERY OF MATERIALS TO SELECTED SINGLE CELLS

BACKGROUND

The disclosure pertains to methods and devices for delivering material to individual selected cells. More particularly, this disclosure is directed to methods for delivering multiple materials and/or multiple doses of the same material to individual cells in a controlled variable manner.

Various methodologies have been proposed for delivering or introducing compounds into selected individual cells. For instance, microinjection techniques employ very small bore needles or micropipettes to manually inject material into the interior of the cell. The microinjection process involves penetration of the cell membrane using a microscope and a finely controlled holder. The holder can be used to place the material in a general region in the cytoplasm. Introduction of the micropipette perturbs the cell membrane and produces mechanical disturbances in the cell interior.

Electroporation is used to introduce agents into a fairly large population of cells in a non-discriminate manner using a transient electric field to produce holes or weaknesses in the cell membrane structure through which the agents may pass. Electro-injection is a combination of microinjection and electroporation in which a transient electric field is used to compromise or open the cell membrane followed by a pressure-driven microinjection procedure to introduce the desired material into the cytoplasm of a selected cell. Both methods involve perturbation of the cell membrane, which can change or alter cellular response to the agent or material under study or analysis. Devices and methodologies which can accurately deliver agents or compounds to targeted single cells either in isolation or in a cellular population in a manner which minimizes or eliminates mechanical or electrical disruption of the cell structure would be desirable.

SUMMARY

Disclosed is a method for delivering material to individual selected cells in which a quantity of fluidizable material is ejected from an electronically controllable fluid delivery device at a velocity and trajectory sufficient to impinge upon the cell membrane in a manner which effects at least one cellular function. Also disclosed is a device for delivering a quantity of at least one compound into contact with at least one cell, the device comprising: a receiving surface adapted to maintain a cell population; and an electronically controllable fluid delivery device associated with the receiving surface, the electronically controllable fluid delivery device targeted to deliver discrete portions of at least one material to the cell.

DESCRIPTION OF THE EMBODIMENTS

Disclosed herein is a method for delivering material to an individual cell. As broadly disclosed, the delivery method involves selecting at least one individual cell and ejecting a quantity of a material from an electronically controllable fluid delivery device. The cell of choice is one bounded by a cell membrane and having an associated cellular volume. The volume of material that is introduced to the selected cell is less than the associated cellular volume. The ejected material travels at a velocity and trajectory sufficient to impinge upon the cell membrane in a manner affecting at least one cellular function.

Figure 1:
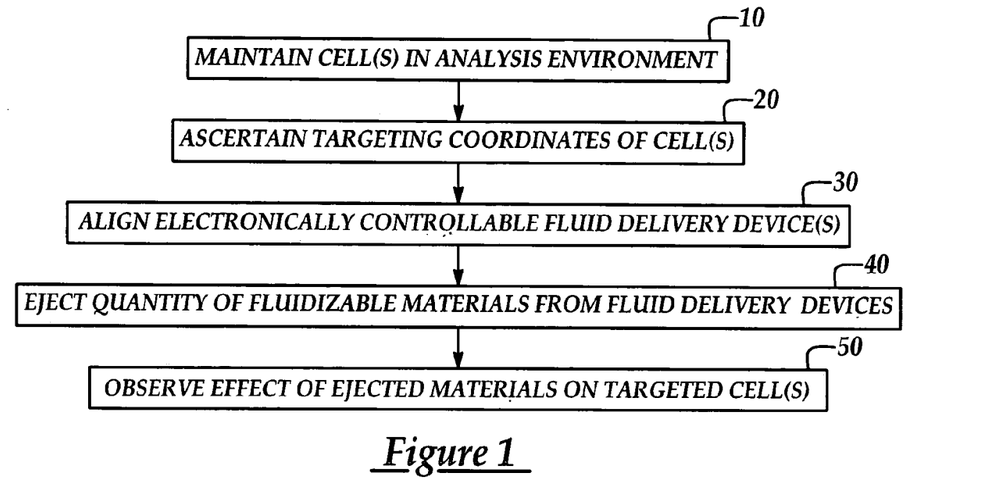
FIG. 1 is a process diagram of a method for delivering material.

A diagram of the method for delivering material to individual selected cells as disclosed herein is set forth in FIG. 1. As used herein, the term "cell(s)" is defined as a biological unit(s) having a volume bounded by a cell membrane. Cells can be prokaryotic or eukaryotic, isolated, or part of a larger population. A cell population can be either homogeneous or heterogeneous depending upon the nature of the tests, processes to be conducted or observed, or procedures to be implemented, etc.

It is also contemplated that the cell(s) may be part of a suitable microcapsule having a given volume, depth, and coordinates. "Microcapsule" as that term is defined herein refers to a device or construct capable of containing and sustaining cell life for a suitable interval. The microcapsule can contain a plurality of cells, biological material and/or other adjunct or auxiliary material and/or devices in a discrete sub-ecology or microfluidic analytic construct.

In the method as disclosed, a quantity of fluidizable material is ejected from an electronically controllable fluid delivery device in a manner which permits the ejected fluidizable material to travel at a velocity and trajectory sufficient to impinge upon the cell membrane of the selected single cell. The quantity of fluidizable material that impinges on the cell membrane is an amount less than the volume of the individual cell.

As used herein, the term "fluidizable material" is defined as a compound or composition that elicits or may elicit a response. The response typically emanates from the cell to which it is introduced. However, the response may be one that is read or discerned in surrounding cells or in the environment surround in the targeted cell or cells. Responses can include, but are not limited to, changes in cell morphology, changes in pigmentation or color distribution, changes in electrochemical response, changes in cytoplasmic function, alteration of protein synthesis or other responses which may be particular to the given cell or cell lines. The fluidizable material may include a bioactive agent or agents of interest or importance. It is also contemplated that the fluidizable material may act as a carrier for other materials to be introduced into contact with a selected cell. Such materials can include, but are not limited to, sub-microscopic electronics, sensors, bio-compatible materials useful as tracers, fiducials and the like.

The fluidizable material may be either a polar or nonpolar substance and may be either organic or aqueous in nature. It is contemplated that the electronically controllable fluid delivery device employed herein will be configured to transfer the fluidizable material of choice in a manner facilitating accurate discrete delivery of the fluidizable material.

"Impingement upon the cell membrane" is employed herein to describe various mechanisms whereby the fluidizable material is associated with the selected cell. Impingement can include contact between the outer cell membrane surface and the ejected quantity of the fluidizable material in a manner whereby at least a portion of the fluidizable material interacts with the cell membrane. Interaction can include, but is not limited to, antigen or immunological responses elicited by interaction between the membrane and the ejected fluidizable material. Impingement can also include the integration of the ejected quantity of fluidizable material into the cell membrane structure either in a multiple step or single step process. It is also contemplated that impingement can further include the movement or transport of the quantity of fluidizable material through the cell membrane into the interior cytoplasm. Movement and/or transport can include the continued transit of the quantity of fluidizable material to sub-cellular structures located within the cell membrane. Impingement is accomplished by contact between the cell membrane and the ejected quantity of fluidizable material in a manner generally permitting continuation of cellular macro-function. Thus, perturbation of the cell membrane due to impact or shear force is minimized in the ejection and introduction event, and cellular function response due to the interaction with or the simple presence of the quantity of fluidizable material can be more readily ascertained and utilized.

It is contemplated that the selected cell or cells can be either isolated or present as members of a given population. The population of cells can be either homogeneous or heterogeneous, depending upon the analysis or process being performed or observed. The cell population (or individual cells) may be prepared, isolated and/or positioned in any suitable manner prior to implementation of the targeting method as disclosed. Thus the population of cells may be collected from any appropriate culture and/or derived by suitable separation or isolation techniques of which flow cytometry is but one non-limiting example.

It is contemplated that targeting a selected cell or cells within a population will provide opportunities for analyzing or exploiting intercellular function as well as intracellular function. Examples of intercellular function processes can include but is not limited to reaction and interaction of non-inoculated cells in response to alteration of processes in the targeted inoculated cell. Thus, information regarding cellular function and process can be derived from direct analysis and observation of the targeted cells or can be inferred from interactions and reactions of associated cells within the population.

Referring now to FIG. 1, the method disclosed herein contemplates that the cell(s) will be maintained in an environment suitable for analysis of at least one cellular function as at reference numeral 10. The environment in which the cell(s) is maintained is contemplated as including materials necessary for sustaining at least one cellular function. Typically it is contemplated that the cellular functions maintained, at minimum, will be those necessary to permit analysis-induced changes in cellular function resulting from the introduction of the ejected material. In a broad sense, the analysis environment is also taken to include adjunct devices facilitating positioning mechanisms and targeting mechanisms used to position the cell(s) and associated support substrate and can serve to target the selected cell(s) relative to the electronically controllable fluid delivery device. Adjunct devices can include, but are not limited to, appropriate micro-movers and other micropositioning devices and mechanisms.

In the method as disclosed, the targeting coordinates of the cell(s) maintained in the analysis environment are as measured and ascertained as at reference numeral 20. Targeting coordinates can include x, y, and z coordinates and can be ascertained by any suitable visual or analytical method including microscopy, scanning electron microscopy, or other visual or visual analog analytical methods.

The electronically controllable fluid delivery device(s) are aligned and positioned as at reference numeral 30. Alignment of electronically controllable fluid delivery device(s) can include, but is not limited to, adjustment and orientation of the electronically controllable fluid delivery device(s) to provide positional targeting relative to the desired cell(s). It is also contemplated that the trajectory of the ejected quantity of fluidizable material may be modified to govern or control delivery of ejected material. Trajectory and hence targeting accuracy and precision can be affected by droplet geometry, temperature and velocity. It is contemplated that the digitally controllable fluid delivery device utilized will be configured to control factors such as droplet geometry, temperature, and/or geometry. Such factors can be governed by numerous mechanisms. By way of example, digitally controllable fluid delivery devices may be configured in a manner similar to that found in inkjet devices and, as such, may have mechanisms and devices that control or modify exit orifice size and/or geometry of an associated ejector. It is also contemplated that other conditions present in the firing chamber of the electronically controllable fluid delivery device that can affect trajectory and targeting can include conditions controlling droplet temperature, velocity, and the like.

The electronically controllable fluid delivery device can be employed independently as a delivery mechanism or can be combined with other devices or accessories as desired or required to delivery material to the cell of choice. It is also contemplated that digital control of the fluid delivery device can permit modification, control, and alteration of the timing of material introduction in a way that will facilitate observation and detection of dose-response.

In the method as disclosed, a quantity of fluidizable material(s) is ejected from the electronically controllable fluid delivery device(s) as at reference numeral 40. The volume of fluidizable material impinging upon the cell membrane will be an amount sufficient to introduce material into contact with the selected cell(s). It is contemplated that a degree of volume reduction may occur between ejection and impingement. Volume reduction may be a result of evaporation or other phenomena. Thus the actual ejection volume may be adjusted to accommodate volume reduction during transit.

The maximum volume of fluidizable material delivered to a selected cell is a volume less than the volume of that cell. Volume control can be accomplished by the control of the droplet size ejected from the fluid delivery device(s). Control of droplet size/volume can be accomplished by various control parameters typically associated with actuation and operation of electronically controllable fluid delivery devices such as various jetting devices as a part of or an adjunct to the targeting operations disclosed.

The electronically controllable fluid delivery device(s) employed in the method as disclosed are those that can provide for generation of droplets and delivery of the generated droplets in a controlled, reproducible, targeted manner over a given distance. As indicated previously, devices having architectures and configurations similar to those typically employed in ink jet technology can accomplish generation and ejection of droplets. Suitable electronically controllable jetting devices are configured to have electronically controllable nozzle members. Electronically controllable jetting devices include, but are not limited to, piezoelectric jetting devices, thermal jetting devices and the like.

The method disclosed also contemplates observation of at least one effect of ejected material(s) on targeted cell(s) as at reference numeral 50. Observation may be for purposes of study, further analysis, or verification of targeting accuracy. Targeting accuracy verification can be accomplished by visual observation and can be augmented by the incorporation of at least one visual enhancement compound into the fluidizable material ejected into contact with the cell(s).

The effect of the ejected material(s) on targeted cell(s) can also include other cellular response mechanisms including, but not limited to, proteomic response patterns, alteration in synthetic process(es) in the cell, changes in membrane permeability, electrochemical alteration(s) occurring in the cell membrane, cytoplasm, cellular organelles or the like. The cellular response mechanism altered, induced, or initiated will vary depending on such factors as the nature of materials employed and the location of the delivery site on the targeted cell.

Cells targeted and treated according to the method disclosed can be subjected to various other post treatment steps and processes. These may include continued observation and analysis, additional targeting and treatment with the same or different agents, and/or separation of targeted cells by suitable separation techniques. To this end, the fluidizable material delivered to targeted cells can include appropriate markers that can assist or facilitate separation processes. Suitable separation technique(s) include, but are not limited to, techniques such as flow cytometry can be used to separate and isolate rare labeled cells.

It is also contemplated that the method disclosed may include multiple targeting operations in which the same or different cells in the cell population can be inoculated with the same or different materials ejected from suitable electronically controllable fluid delivery devices. Thus the method disclosed contemplates staged multiple delivery of a material or materials to selected cell(s) in multiple steps.

The method as disclosed herein can include the further step of ascertaining delivery accuracy. Ascertainment of delivery accuracy of the fluidizable material to the selected cell(s) can be accomplished by any various methods. Observation of the effect of ejected materials on targeted cell(s) can, in some instances, be inferentially employed to ascertain targeting accuracy. Thus, alterations in cell membrane, transport characteristics, pigmentation, or other physical, physical-chemical, chemical or biochemical alterations can be employed as indicia of targeting accuracy. It is also contemplated that the fluidizable material being ejected can include at least one visualization enhancement compound. The visualization enhancement compound can be any material, compound, marker or the like which would enable visualization by an appropriate device or detector. One such non-limiting example is a fluorophore.

Given targeting accuracy and precision, it is contemplated that the method as disclosed can be employed to deliver fluidizable material or materials to multiple locations defined in or on a selected cell. Thus, the method as disclosed can include delivery of materials to selected cell(s) as well as delivery of material to one or more specific locations on a given cell or cells. The ability to target and deliver fluidizable material to specific locations on a given cell or cells can permit observation and utilization of localized response to the given material and stimulus. Such localized responses manifest as changes in cell morphology, and the like, and can be suitable for data clustering analysis and other analytical methodologies.

The targeted delivery method as disclosed can be employed in tandem with various other biosynthetic and/or biomanipulative processes. The targeted delivery method can be utilized to implement various standard recombinant culture techniques typically employed on a culture-wide basis. Unlike prior procedures which required manipulation of cell cultures having hundreds or more cells, the method disclosed herein permits recombinant culture techniques to be performed on a cell-by-cell basis. Thus materials such as recombinant DNA for gene therapy can be delivered to cells in a precise manner. It is contemplated that the method as disclosed can be employed in tandem with suitable flow cytometric techniques. Rare cell lines isolated by the flow cytometric processes can be injected or impinged with material as they are sorted creating a continuous or quasi-continuous process. It is also contemplated that the method as disclosed can be adapted to various proteomic techniques.

The delivery method as disclosed can encompass precise control of substrate-to-delivery device distance. Such control can be accomplished by any suitable mechanism such as a spacer. Controlled distance, either alone or in combination with kinetic energy provided to the ejected droplet as a result of residence and exit from the electronically controllable fluid delivery device can be manipulated to effect velocity of the droplet. Thus, the velocity can be mediated by modification of at least one of space or kinetic energy imparted to deliver a droplet in a manner to permit impingement upon the cell membrane.

Substrate-to-delivery device distance is also determined to achieve optimum temperature of the droplets at the impingement event. Without being bound to any theory, it is believed that impingement as that term is employed herein is a function of multiple factors including trajectory of the droplet, velocity of the droplet, size and geometry of the droplet, and temperature of droplet at impingement. In certain instances, subtle variations in temperature at impingement can permit integration of the droplet into or transfer of the droplet through the cell membrane. The droplet temperature will generally approximate the temperature of the targeted cell with upper and lower maximums being defined at levels that will not adversely affect or disrupt function of the targeted cell(s).

In the method disclosed, the droplet temperature can be controlled and adjusted by any suitable method. One suitable method is by residence in the electronically controllable fluid delivery device. Suitable electronically controllable fluid delivery devices can include heating devices that provide and regulate the temperature of the material resident in the associated ejection chamber, either directly or indirectly. Such heating devices can include, for example, resistors as would be employed in a thermal jetting device. Specific control of the distance between the substrate and the jetting device can also be employed to deliver material to the cell at a temperature that maximizes the ability of the material to be received into the cell or onto the cell membrane as desired or required.

Cell membrane structure exhibits a degree of porosity and permeability. It is believed that material administered at a precise microdosage quantity, delivered at specific velocities and controlled temperatures can synchronize with the permeability of the cell membrane to permit residence of the material on the cell membrane and/or transit of the delivered material through the membrane to the desired location within the cell. It is further contemplated that such permeability may be either uniform or site specific on the cell membrane. Thus, controlled accuracy in the application of material to a specific site can also be utilized to permit introduction of the desired material in a manner that does not unduly perturb or compromise the membrane and associated cellular function.

The method disclosed herein contemplates that the electronically controllable fluid delivery device is positioned a spaced distance from the target region such that the ejected material travels through a distant region prior to impingement. It can be appreciated that a spaced distinct region composed of a suitable gas or the like can minimize sample bleeding or diffusion. In instances such as non-liquid to liquid contact between polar to nonpolar materials, immiscibility factors can prevent or minimize material bleeding and thus can permit a contact situation.

The method disclosed herein also contemplates that the fluidizable material can be ejected and applied to large arrays of selected cells for large-scale production or processing. Thus, it is contemplated that high throughput cellular testing, screening and analysis can be achieved.

The method also contemplates that multiple materials can be delivered to selected cell(s). Multiple materials can be delivered either simultaneously or sequentially to selected cells. It is contemplated that the selected individual cells can be the same cells or different cells within the population. Thus, if multiple materials are delivered to the same cell, it is within the purview of this method to deliver the materials to proximate or distal sites on the cell membrane. It is also contemplated that delivery of materials to different cells within the population can be utilized to observe various interactive effects.

Material(s) can be delivered contemporaneously, i.e. materials can be delivered from multiple controllable fluid delivery devices during time intervals deemed to be essentially contemporaneous. It is also contemplated that various materials can be delivered sequentially in any fashion facilitating the analysis or process being undertaken. Where the material is delivered to different cells within the population, it is also contemplated that a suitable identification and targeting hierarchies can be employed to identify the different cells for targeted delivery. Such identification hierarchies can include cell morphology identification as well as various forms of protein analysis, marker identification and the like. It is contemplated that identification routines can include appropriate automated morphology recognition algorithms and protocols as well as radiological and/or immunological marker or tracer uptake methodologies.

Thus, the method as disclosed also contemplates delivering material or materials to individual selected cells having internal volumes bounded by cell membranes.

The method disclosed herein also broadly includes the step of ejecting controllably variable quantities of at least a first fluidizable material and a second fluidizable material from associated electronically controllable fluid delivery devices such as electronically controllable jetting devices. These materials can differ from one another in composition, activity or other suitable characteristics or qualities. The ejected quantities of each of the fluidizable materials travel at velocities and trajectories sufficient to impinge upon the membranes of the targeted cells in a manner effecting at least one cellular function. While the method is described in terms of first and second fluidizable materials, the method contemplates the use of any number of variations of fluidizable materials.

It is contemplated that the quantity of first and second fluidizable material can be controllably variable. Controlled variability can be accomplished by multiple administrations of one or more fluidizable materials to a selected cell over time. It is also contemplated that the size/volume of the ejected droplet can be varied to alter quantity. Maximum droplet size would be a volume less than the size of the volume of the cell to which the material is to be delivered. Where multiple droplets are introduced into contact with a single cell, it is contemplated that the total volume of the introduced materials will be such that the utility of cell function is not unduly compromised.

Controlled variability can be governed by suitable control commands developed by users to create the desired observational array. Additionally, controlled variability can be governed by calculations that alter or govern the timing, velocity, trajectory, temperature and other physical characteristics of the ejected droplets. It is also contemplated that controlled variability can be a function any or all of the aforementioned considerations.

The ejected quantity of at least one of the fluidizable materials volume can be introduced at a targeted location within cellular cytoplasm in a manner that permits cellular macrofunction. It is contemplated that at least one of the fluidizable materials can be introduced to a location such as a subcellular organelle located within the cellular cytoplasm. The manner of delivery and introduction is one that minimizes the disruption to the cell so targeted. "Cellular macrofunction" is defined as general cellular processes that occur to maintain cellular function. It is understood that introduction of the fluidizable material or materials can cause some alteration in cellular function. This alteration can, in some instances, lead to cell death. However, the method of delivery is one that will minimize perturbation due to impingement in delivery to permit more unimpeded observation and study of the interaction between the cellular system and the introduced material.

It is also contemplated that the ejected quantity of at least one fluidizable material can be integrated onto a target location on a surface of the cell membrane. Thus, the material may be one which has an affinity or can be made to have an affinity with the cell membrane causing changes in membranes' structure, function or the like. Thus, it is contemplated that, where multiple materials are employed, a material may be integrated into the cell membrane which can alter localized regions of the cell membrane facilitating subsequent introduction of an additional fluidizable material into the cellular cytoplasm or the like.

It is also contemplated that at least one fluidizable material can be ejected at a velocity and trajectory suitable to deliver the quantity of fluidizable material to a specified location within the cellular cytoplasm. As indicated previously, control of velocity and trajectory can be a function of spacing between the electronically controllable jetting devices and the targeted cell as well as ejection kinetics and the like.

The method contemplates an additional step in which the accuracy of delivery of the fluidizable materials is ascertained. Delivery accuracy can be ascertained by any direct or indirect method including visual observation and/or sensor modification, as well as dose response observation. In order to further ascertain accuracy of delivery, it is contemplated that the fluidizable material can include at least one visualization enhancement compound. Such an enhancement compound can be a radiological or chemical marker that can be analyzed and detected by a suitable detection mechanism or methodology. Determination of delivery accuracy can include both the determination that a material has been brought into contact with a given cell and the ascertainment of locational accuracy on the cell membrane or within the cell volume itself. As desired or required, the fluidizable material can include appropriate affinity markers and the like which would assist in determining that a quantity of fluidizable material was accurately delivered to a location on or in the cell of choice.

The method disclosed can include the additional step of separating the cell from an associated cellular population subsequent to impingement of at least one fluidizable material. Separation can occur by any suitable means such as flow cytometry or the like. It is contemplated that separation can occur after impingement of one or more of the fluidizable materials. Thus, the method further contemplates a multistep process in which a fluidizable material or materials are impinged upon a cell in a cell population after which separation techniques are implemented and further impingement of fluidizable materials can occur as desired or required.

Figure 2:
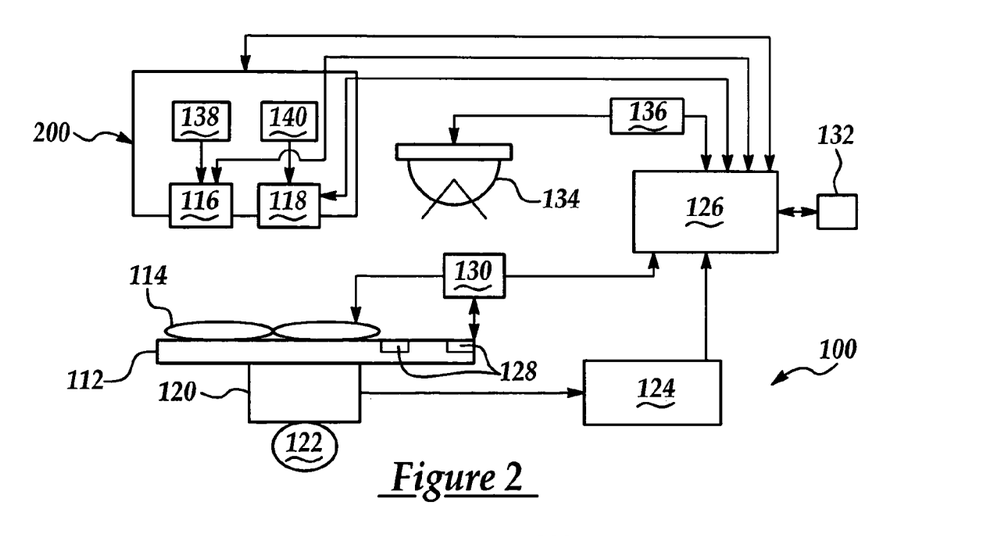
FIG. 2 is a schematic diagram of a device for delivering material to single cells.

Also disclosed is a device 100 for delivering quantities of at least one compound to at least one cell in a population. One such device is schematically depicted in FIG. 2. The device includes a receiving surface 112 adapted to maintain the cell or cell population 114 and an electronically controlled fluid delivery device 116, 118 targeted to deliver discrete portions of at least one material to a cell 114 positioned on receiving surface 112. The receiving surface 112 is configured to maintain the cell or cell population 114 in a viable or suitable state appropriate for analysis or manipulation as desired or required. Thus, the receiving surface 112 can include appropriate nutrients and support mechanisms to maintain the cells in a viable functional condition.

Additionally, the receiving surface 112 can be mounted on or connected to an appropriate support device 120 that can cooperatively interact with the electronically controllable fluid delivery device 116, 118 to accomplish positioning of the targeted cells 114 and electronically controllable fluid delivery device 116, 118 in a manner that facilitates accurate delivery of the ejected material or materials. Cooperative interaction can include moveable positioning of the receiving surface 112, associated with the support surface 120, as well as interactive analysis and input of the support surface 112 and cell(s) 114 relative to support device 120. The underlying support device 120 can be a suitable precision accurate locational device configured with appropriate motors, positional variation devices and the like as indicated at 122. Non-limiting examples of such precision accurate locational devices include mechanisms having stepper motors, encoders, linear induction motors and the like capable of achieving incremental movement appropriate for addressing the targeted cell.

The underlying support 120 can be in communication with an appropriate adjustment controller 124 to accomplish positional adjustment of support surface 112. Positional adjustment generally occurs in the x and y planes to permit scanning movement relative to electronically controllable fluid delivery device 116, 118. However, it is also contemplated that the support surface 112 can be adjusted in spaced relationship to the electronically controllable fluid delivery device 116, 118 to adjust or alter the distance between the electronically controllable fluid delivery device and cell 114.

Suitable adjustment of the support surface 112 as accomplished by underlying support 120 is governed by support control mechanism 124. The device will include suitable electronic control mechanisms to accomplish such electronic control. It is contemplated that the support surface control mechanism 124 can also be in electronic communication with a central ejection control device 126 configured to govern various functions related to the operation of the associated electronically controllable fluid delivery devices 116, 118.

The support surface 112 can be composed of any suitable material or materials necessary to provide or maintain cellular function. It is also contemplated that the support surface 112 can include contacts and leads 128 which are capable of monitoring at least one cellular function exhibited by cell(s) 114. The leads 128 can communicate with an appropriate sensor mechanism or array 130 which can monitor at least one cellular function or response. It is also contemplated that the sensor mechanism 130 can include leads, probes or the like which are capable of direct communication with a cell or cells in the population. Additionally, the sensor mechanism 130 can be configured to indirectly monitor cellular response by means of environmental testing and the like. Sensor mechanism 130 can be placed in electronic communication with controller 126 if desired or required. It is understood that the sensor mechanism 130 can include an array of sensor devices capable of detecting one or more physical and/or chemical or other responses. The array of sensor devices can include devices that are identical, similar or different as desired or required to detect and/or quantify various responses of interest.

The device 100 can also include a suitable actuator capable of triggering ejection of at least one material from the electronically controllable fluid delivery device 116, 118 such as a jetting device to impinge on the targeted cell 114 present on receiving surface 112. As depicted in FIG. 2, the actuator 132 can be in electronic communication with the controller 126 to govern actuation of the electronically controllable fluid delivery device 116, 118. It is contemplated that the actuator 132 can be included in an appropriate interface array that will permit interaction with external sources and/or operators.

The controller 126 is capable of interactive electronic communication with various elements such as the support surface control 124, sensor 130, and actuator 132. It is also contemplated that the controller or other suitable device can provide at least one signal which governs operation of the electronically controllable fluid delivery device in a manner which effects at least one of ejected droplet size, droplet velocity, droplet temperature, and droplet trajectory.

It is also contemplated that the electronically controllable fluid delivery device 116, 118 can include an appropriate heating mechanism capable of heating the material delivered to the cell. While a variety of heating devices can be employed, it is contemplated that heating can occur by means of a resistor integrated into the firing chamber of electronically controllable jetting devices such as thermal jetting devices.

The electronically controllable fluid delivery device 116, 118 can be any suitable device that can be configured to emit discrete droplets of material in a volume that is less than the volume of the targeted cell 114. Suitable devices can include jetting devices typically referred to as piezoelectric actuated jetting devices and thermal actuated jetting devices.

The device 100 can also include a targeting adjustment mechanism associated with the electronically controllable fluid delivery device 116, 118. As depicted in FIG. 2, it is contemplated that the targeting adjustment mechanism can be an electronically governed system controlled by controller 126 capable of moveably positioning the electronically controllable fluid delivery device 116, 118 relative to the receiving surface 112. In this manner, the electronically controllable fluid delivery device 116, 118 can be positioned with respect to the receiving surface 112, and cells 114 positioned thereon. It is contemplated that the distance or space between the membrane surface of cell 114 and the electronically controllable fluid delivery device 116, 118 can be altered to insure proper impingement of the quantity of material ejected from the particular fluid delivery device.

It is contemplated that the device 100 can include appropriate sensors and control devices to accurately adjust the spaced distance between the membrane surface of cell 114 and the exit orifice of the electronically controllable fluid delivery device 116, 118 to ensure appropriate impingement of the ejected quantity of material relative to the cell membrane.

The device 100 can also include appropriate analytical and/or observational tools suitable for observing the cells 114 and observing and/or recording any alterations in cell function subsequent to impingement of the ejected material. Various investigational devices can be utilized in the device as disclosed herein. One such device as presented in FIG. 2 is optic scanner 134. As depicted in FIG. 2, optic scanner 134 is in electronic communication with controller 126 through data acquisition interface 136. The optic scanner 134 or other suitable investigational device is adapted to detect at least one alteration in cellular function manifested as a result of the introduction of the defined quantity of fluidizable material into cell 114 from electronically controllable fluid delivery device 116, 118. The optic scanner or other suitable investigational device can be any suitable device capable of observing and/or analyzing such induced changes in cellular function.

It is contemplated that the investigational device such as optic scanner 134 can be permanently associated with the delivery device 100. It is also contemplated that the investigational device such as optic scanner 134 can be removably connected to the delivery device 100 such that a variety of different investigational devices can be employed depending upon the nature of the selected cell 114 and the type of analysis being performed.

Electronically controllable fluid delivery devices 116, 118 can be associated with any suitable source or material. It is contemplated that the material sources or reservoirs may be remote from the delivery device 100. It is also contemplated that suitable storage reservoir(s) 138, 140 can be located proximate to associated electronically controllable fluid delivery devices 116, 118. It is contemplated that the material contained in one or more reservoirs 138, 140 can include various bioactive agents. These agents can be chemicals, compounds or compositions that can exert or induce a cellular response when brought in contact with the cell 114. The electronically controllable fluid delivery devices 116, 118 can be permanently associated with the delivery device 100 if desired or required.

Figure 3:
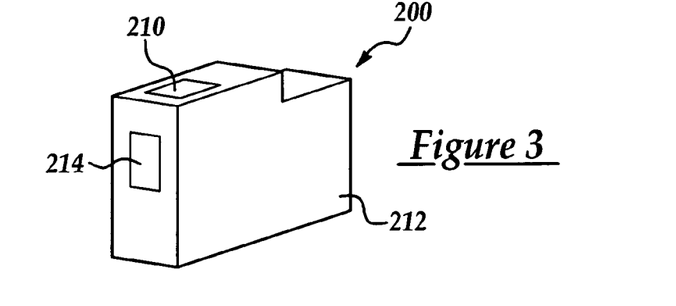
FIG. 3 is a perspective view of a cartridge for use with the delivery device of FIG. 2.

It is also contemplated that the electronically controllable delivery devices 116, 118 and associated storage reservoirs 138, 140 can be configured into a cartridge 200 which can be removably positioned in device 100. The cartridge 200 as depicted in FIGS. 2 and 3 includes a reservoir for containing a volume material and an electronically controllable drop ejection device in communication with the reservoir. The electronically controllable drop ejection device can be configured as print head 210 positioned on housing 212. The cartridge can also include an appropriate memory device 214 containing information relative to bioactive material contained in the reservoir. The memory device 214 can be configured to be capable of electronic communication with an external source such as controller 126.

It is contemplated that the device 100 can be employed in a method for ascertaining response in an individual cell or cells. Such response method would include the steps of delivering the defined volume of at least one bioactive material to at least one cell positioned on a receiving surface in which the bioactive material is dispensed for delivery by at least one electronically controllable fluid delivery device.

As used herein the term "bioactive material" includes materials having a detectable effect on a cell or cells as well as those believed to have such an effect. The cellular response exhibited subsequent to the delivery of the defined volume of bioactive material can be observed and recorded. Such bioactive material is delivered at a trajectory and a velocity sufficient to achieve impingement of the defined volume of bioactive material with the cell membrane of the cell. Impingement can include association with the membrane surface a well as transit through the membrane to the cytoplasm and/or cellular organelles contained therein. The material or materials delivered to the targeted cell can include various materials that can assist in the visualization of the cellular response and/or the ascertainment of targeting accuracy. It is contemplated that the defined volume of the bioactive material will be a volume less than the total cellular volume. Furthermore, it is contemplated that the bioactive material can be delivered to multiple locations defined within or on the cell. Such delivery can be simultaneous or sequential depending upon the nature of the observation as desired.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A method for delivering material to an individual cell, the cell having a volume bounded by a cell membrane, the method comprising the steps of:

selecting the individual cell, the cell being disposed on a receiving surface adapted to maintain a cell population, wherein the receiving surface has at least one planar support surface adapted to receivably position the individual cell thereon, wherein the planar support surface includes at least one sensor associated therewith; and ejecting a quantity of a material from an electronically controllable fluid delivery device associated with the receiving surface, the electronically controllable fluid delivery device targeted to deliver discrete portions of the material to the cell, the quantity of material being less than the volume of the individual cell, the ejected material traveling at a velocity and trajectory sufficient to impinge upon the cell membrane in a manner which affects at least one cellular function.

2. The method of claim 1, further comprising the step of maintaining the individual cell in an environment suitable for analysis of at least one cellular function.

3. The method of claim 2 wherein the individual cell is maintained in a microcapsule.

4. The method of claim 1 wherein the ejected quantity of material is introduced within cellular cytoplasm.

5. The method of claim 1 wherein the ejected quantity of material is associated onto an exterior surface of the cell membrane.

6. The method of claim 1 wherein the ejected quantity of material impinges on the cell membrane in a manner permitting continuation of cellular macrofunction.

7. The method of claim 1 wherein the ejected quantity of material is ejected at a velocity and trajectory suitable to deliver the quantity of material to a specified location within the cell volume.

8. The method of claim 1 wherein the method further comprises the step of ascertaining accuracy of delivery of material to the cell.

9. The method of claim 8 wherein the material includes at least one visualization enhancement compound.

10. The method of claim 1 wherein the selected cell is a member of a population of cells.

11. The method of claim 10 wherein the selected cell is a member of a homogeneous population.

12. The method of claim 10 wherein the selected cell is a member of a heterogeneous population.

13. The method of claim 10, further comprising the step of separating the cell from the population subsequent to impingement of the material.

14. The method of claim 1 wherein the material is delivered to multiple locations defined in the cell.

15. The method of claim 1 wherein the material includes at least one bioactive compound.

16. A method for delivering materials to individual selected cells, the cells having internal volumes bounded by cell membranes, the method comprising the steps of:
   selecting the individual cells, the individual cells being disposed on a receiving surface adapted to maintain a cell population, wherein the receiving surface has at least one planar support surface adapted to receivably position the individual cells thereon, wherein the planar support surface includes at least one sensor associated therewith; and
   ejecting controllably variable quantities of a first material and a second material from electronically controllable fluid delivery devices associated with the receiving surface, the electronically controllable fluid deliver devices targeted to deliver discrete portions of the first and second materials to the selected individual cells, the ejected quantities of materials traveling at a velocity and trajectory sufficient to impinge upon the cell membranes in a manner which affects at least one cellular function.

17. The method of claim 16 wherein the ejected quantity of at least one of the first or second materials is introduced at a targeted location within cellular cytoplasm in a manner that permits continuation of cellular macrofunction.

18. The method of claim 16 wherein the ejected quantity of at least one of the first or second materials is affixed onto a targeted location on an exterior surface of the cell membranes in a manner that permits continuation of cellular macrofunction.

19. The method of claim 16 wherein the ejected quantity of at least one of the first or second materials is ejected at a velocity and trajectory suitable to deliver the quantity of the at least one of the first or second materials to a specified location within cellular cytoplasm.

20. The method of claim 16 wherein the method further comprises the step of ascertaining accuracy of delivery of the materials to the cells.

21. The method of claim 20 wherein at least one of the first or second materials includes at least one visualization enhancement compound.

22. The method of claim 20, further comprising the step of ascertaining locational accuracy of the elected materials within the cells.

23. The method of claim 22 wherein at least one of the first and second materials includes at least one visualization enhancement compound.

24. The method of claim 16, further comprising the step of separating the cells from an associated cellular population subsequent to impingement of at least one of the first or second materials.

25. A device for delivering quantities of at least one compound to at least one cell in a population, the device comprising:
   a receiving surface adapted to maintain a cell population;
   an electronically controllable fluid delivery device associated with the receiving surface, the electronically controllable fluid delivery device targeted to deliver discrete portions of at least one material to the cell; and
   at least one sensor mechanism, the sensor mechanism configured to monitor at least one cellular response mechanism exhibited by at least one cell positioned on the receiving surface.

26. The device of claim 25, further comprising an actuator capable of triggering ejection of at least one material from the electronically controllable fluid delivery device to impinge on the cell on the receiving surface.

27. The device of claim 25 wherein the receiving surface is positioned on a support member, the support member having a movement mechanism capable of orienting the receiving surface relative to the electronically controllable delivery device.

28. The device of claim 25 wherein the receiving surface has at least one planar support surface adapted to receivably position at least one cell thereon.

29. The device of claim 28 wherein the planar support surface is adapted to maintain and position at least one cell population.

30. A device for delivering quantities of at least one compound to at least one cell in a population, the device comprising:
   a receiving surface adapted to maintain a cell population; and
   an electronically controllable fluid delivery device associated with the receiving surface, the electronically controllable fluid delivery device targeted to deliver discrete portions of at least one material to the cell;
   wherein the receiving surface has at least one planar support surface adapted to receivably position at least one cell thereon, and wherein the planar support surface includes at least one sensor associated therewith.

31. The device of claim 25 wherein the sensor mechanism comprises a plurality of sensors, the plurality of sensors capable of selecting at least two differing cellular responses, the cellular responses including at least one of a physical response or a chemical response.

32. The device of claim 25 further comprising a controller in electronic communication with the electronically controllable fluid delivery device, the controller configured to emit at least one signal governing operation of the electronically controllable fluid delivery device.

33. The device of claim 32 further comprising an actuator in electronic communication with the controller to govern actuation of the electronically controllable fluid delivery device.

34. The device of claim 32 wherein the signal governing operation of the electronically controllable fluid delivery device operates in a manner which affects at least one of droplet size, droplet velocity, droplet temperature, and or droplet trajectory.

35. The device of claim 25 wherein the electronically controllable fluid delivery device is a jetting device and further comprises a heating mechanism the heating mechanism capable of heating the material delivered to the cell.

36. The device of claim 25 wherein the electronically controllable jetting device is a piezoelectric jetting device.

37. The device of claim 25 wherein the electronically controllable jetting device is a thermal jetting device.

38. The device of claim 25 further comprising a targeting adjustment mechanism associated with the electronically controllable fluid delivery device, the targeting adjustment mechanism capable of movably positioning the electronically controllable fluid delivery device relative to the receiving surface.

39. The device of claim 38 wherein the electronically controllable fluid delivery device is movably positionable with respect to distance to the receiving surface.

40. A device for delivering quantities of at least one compound to at least one cell in a population, the device comprising:
- a receiving surface adapted to maintain a cell population;
- an electronically controllable fluid delivery device associated with the receiving surface, the electronically controllable fluid delivery device targeted to deliver discrete portions of at least one material to the cell; and
- an investigational device adapted to detect at least one alteration in cellular function manifested in the cell as a result of impingement of the discrete quantity of material to the cell.

41. A device for delivering quantities of at least one compound to at least one cell in a population, the device comprising:
- a receiving surface adapted to maintain a cell population;
- an electronically controllable fluid delivery device associated with the receiving surface, the electronically controllable fluid delivery device targeted to deliver discrete portions of at least one material to the cell;
- a targeting adjustment mechanism associated with the electronically controllable fluid delivery device, the targeting adjustment mechanism capable of movably positioning the electronically controllable fluid delivery device relative to the receiving surface; and
- at least one memory device capable of electronic communication with an external source, the memory device containing information relevant to bioactive material contained in the reservoir.

42. A method for ascertaining response in an individual cell, the method comprising:
- delivering a defined volume of at least one bioactive material to at least one cell, the at least one cell disposed on a receiving surface adapted to maintain a cell population, wherein the receiving surface has at least one planar support surface adapted to receivably position the individual cell thereon, wherein the planar support surface includes at least one sensor associated therewith, the bioactive material being dispensed for delivery by at least one electronically controllable fluid jetting device associated with the receiving surface, the electronically controllable fluid jetting device targeted to deliver discrete portions of the at least one bioactive material to the at least one cell; and
- observing and recording cellular response subsequent to the delivery of the defined volume of bioactive material.

43. The method of claim 42 wherein the bioactive material is delivered at a trajectory and velocity sufficient to achieve impingement of the defined volume of bioactive material with the cell membrane of the cell.

44. A device for delivering material to a single cell, comprising:
- means for selecting the single cell;
- means for electronically controllably jetting a quantity of material from a reservoir into contact with the selected cell at a velocity and trajectory sufficient to impinge on the cell; and
- means for monitoring at least one cellular response mechanism exhibited by at least one cell positioned on the receiving surface.

\* \* \* \* \*

UNITED STATES PATENT AND TRADEMARK OFFICE
CERTIFICATE OF CORRECTION

PATENT NO. : 7,132,242 B2
APPLICATION NO. : 10/704993
DATED : November 7, 2006
INVENTOR(S) : Paul H. McClelland et al.

It is certified that error appears in the above-identified patent and that said Letters Patent is hereby corrected as shown below:

In column 13, line 63, in Claim 22, delete "elected" and insert -- ejected --, therefor.

In column 14, line 62, in Claim 34, after "temperature," delete "and".

In column 14, line 66, in Claim 35, insert -- , -- before "the heating".

Signed and Sealed this

Fourteenth Day of April, 2009

JOHN DOLL
*Acting Director of the United States Patent and Trademark Office*